United States Patent
Rousseau (10) Patent No.: US 8,821,539 B2
(45) Date of Patent: Sep. 2, 2014

(54) COLLAPSIBLE BARBED SUTURES HAVING REDUCED DRAG AND METHODS THEREFOR

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 1190 days.

(21) Appl. No.: 12/177,947

(22) Filed: Jul. 23, 2008

(65) Prior Publication Data
US 2010/0023055 A1 Jan. 28, 2010

(51) Int. Cl.
A61B 17/04 (2006.01)
A61B 17/06 (2006.01)
A61B 17/00 (2006.01)

(52) U.S. Cl.
CPC . *A61B 17/06166* (2013.01); *A61B 2017/00526* (2013.01); *A61B 2017/06176* (2013.01)
USPC .......................................................... 606/228

(58) Field of Classification Search
USPC ............ 606/228, 229, 230, 231; 24/449, 450, 24/451, 452; 57/200; 264/177.13
See application file for complete search history.

(56) References Cited

U.S. PATENT DOCUMENTS

| | | | |
|---|---|---|---|
| 3,072,986 A | 1/1963 | Lafnaer | |
| 3,123,077 A | 3/1964 | Alcamo | |
| 3,463,436 A | 8/1969 | Foster | |
| 3,570,497 A | 3/1971 | Lemole | |
| 3,833,972 A * | 9/1974 | Brumlik | 24/449 |
| 3,981,051 A * | 9/1976 | Brumlik | 24/447 |
| 4,069,825 A | 1/1978 | Akiyama | |
| 4,950,285 A | 8/1990 | Wilk | |
| 5,053,047 A | 10/1991 | Yoon | |
| 5,074,874 A | 12/1991 | Yoon et al. | |
| 5,123,913 A | 6/1992 | Wilk et al. | |
| 5,500,000 A | 3/1996 | Feagin et al. | |
| 5,531,761 A | 7/1996 | Yoon | |
| 5,549,619 A | 8/1996 | Peters et al. | |
| 5,643,295 A | 7/1997 | Yoon | |
| 5,665,109 A | 9/1997 | Yoon | |
| 5,683,417 A | 11/1997 | Cooper | |
| 5,919,233 A | 7/1999 | Knopf et al. | |
| 5,931,855 A | 8/1999 | Buncke | |
| 6,848,152 B2 * | 2/2005 | Genova et al. | 29/7.1 |
| 7,021,316 B2 | 4/2006 | Leiboff | |
| 7,125,413 B2 | 10/2006 | Grigoryants et al. | |

(Continued)

FOREIGN PATENT DOCUMENTS

| | | |
|---|---|---|
| DE | 102005004317 B3 | 6/2006 |
| EP | 1929961 A2 | 6/2008 |
| WO | WO 2009097556 A2 | 8/2009 |
| WO | WO 2009129251 A2 | 10/2009 |

*Primary Examiner* — Corrine M McDermott
*Assistant Examiner* — Jing Ou (57) ABSTRACT

A barbed suture includes a flexible thread having a core with a leading end, a trailing end, and a central axis. The barbed suture includes a first flexible flap connected to the core, the first flap extending between the leading and trailing ends of the core, and a second flexible flap connected to the core, the second flap extending between the leading and trailing ends of the core. The flexible flaps and the core have an S-shaped profile when viewed in cross-section. The barbed suture includes first and second slots formed in the respective first and second flaps for dividing the flaps into first and second barbs projecting from the core, whereby each slot extends outwardly from the core and rearwardly toward the trailing end of the core.

20 Claims, 4 Drawing Sheets

(56) References Cited

U.S. PATENT DOCUMENTS

| | | | |
|---|---|---|---|
| 2003/0149447 A1* | 8/2003 | Morency et al. | 606/228 |
| 2007/0005109 A1* | 1/2007 | Popadiuk et al. | 606/228 |
| 2007/0005110 A1 | 1/2007 | Collier et al. | |
| 2007/0038249 A1* | 2/2007 | Kolster | 606/228 |
| 2007/0239207 A1* | 10/2007 | Beramendi | 606/228 |
| 2009/0043336 A1* | 2/2009 | Yuan et al. | 606/228 |

* cited by examiner

COLLAPSIBLE BARBED SUTURES HAVING REDUCED DRAG AND METHODS THEREFOR

CROSS REFERENCE TO RELATED APPLICATIONS

The present invention is related to commonly assigned U.S. patent application Ser. No. 12/135,176, filed Jun. 7, 2008, and Ser. No. 12/140,311, filed Jun. 17, 2008, now U.S. Pat. No. 8,100,941 the disclosures of which are hereby incorporated by reference herein.

BACKGROUND OF THE INVENTION

1. Field of the Invention

The present invention generally relates to surgical sutures, and more specifically relates to surgical sutures having projecting barbs used for anchoring the sutures in tissue and prosthetic devices.

2. Description of the Related Art

Surgical sutures are used for closing wounds and surgical incisions, and repairing damaged muscles, vessels, and tissue. Typically, a needle is attached to one end of the suture, and the needle is drawn through tissue to form one or more loops holding the tissue together. The suture is subsequently tied off in one or more knots so that the tissue will remain drawn together, or so that a prosthetic device will remain anchored in place.

Although sutures are very effective for closing wounds and incisions, there are a number of problems associated with conventional sutures. Many of these problems are directly related to the knots used to secure sutures in place. If the knots are not tied properly, defects may arise including slippage, knot breakage, and re-opening of the wound or incision. In addition, using knots to secure sutures may distort tissue, restrict blood flow, increase the formation of scars, impede wound healing, and result in infection.

In response to the deficiencies associated with conventional sutures, barbed sutures have been developed. Unlike conventional sutures, barbed sutures have projecting barbs that allow the suture to be used to close wounds, approximate tissue, tighten tissue, and attach prosthetic devices without using knots. U.S. Pat. No. 5,931,855 discloses a barbed suture that is used for cosmetic procedures such as brow-lifts and face-lifts.

Figure 1:
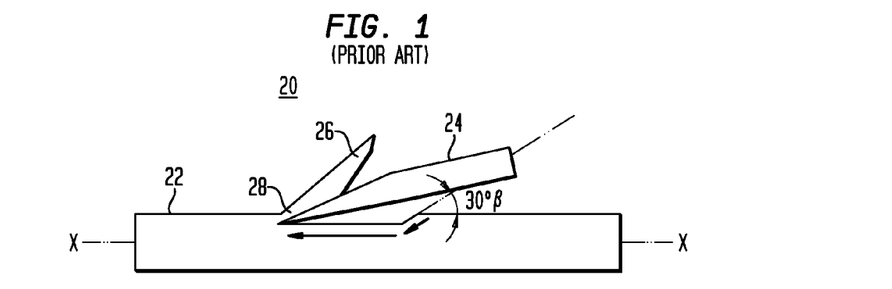
FIG. 1 shows a prior art method of making a barbed suture.

Referring to FIG. 1, a conventional barbed suture 20 is generally formed by cutting a core thread 22 with a cutting blade 24. FIG. 1 illustrates an exemplary cut, whereby the cutting blade 24 first cuts into the core thread 22 at an angle β of approximately 30 degrees relative to a longitudinal axis x-x of the core thread to a depth of approximately 0.008 inches, and subsequently further cuts into the core thread for a distance of approximately 0.024 inches at an angle of approximately 0 degrees to form a projecting barb 26. After the cut is completed, the barb 26 remains connected to the core thread 22 through a base 28.

Performing a barb-cutting operation as shown in FIG. 1 requires the use of a mechanical shearing methodology that will rapidly dull the cutting edge of the cutting blade, thereby requiring frequent changes of the cutting blade. The cutting methodology is also negatively affected by the typical extruded diameter variation in the target thread. This variation in diameter requires a cutting head that must be frequently adjusted in fine diameter threads as small changes in thread diameter result in significantly thinner/weaker barbs, or in thicker threads resulting in thicker, stiffer barbs that will cause a variation in frictional drag during application.

The leading edge of the cuts in the core thread act as stress concentration points. In applications where a significant or pulsatile load is placed on the barbed suture, e.g., heart valve repair or replacement procedures and orthopedic applications, a given barb may fail, or begin peeling away from the core thread. Once this occurs, due to the highly oriented nature of the suture material, the barb may be stripped off the core thread along a significant length of the suture causing catastrophic failure of the suture approximation.

Figure 2:
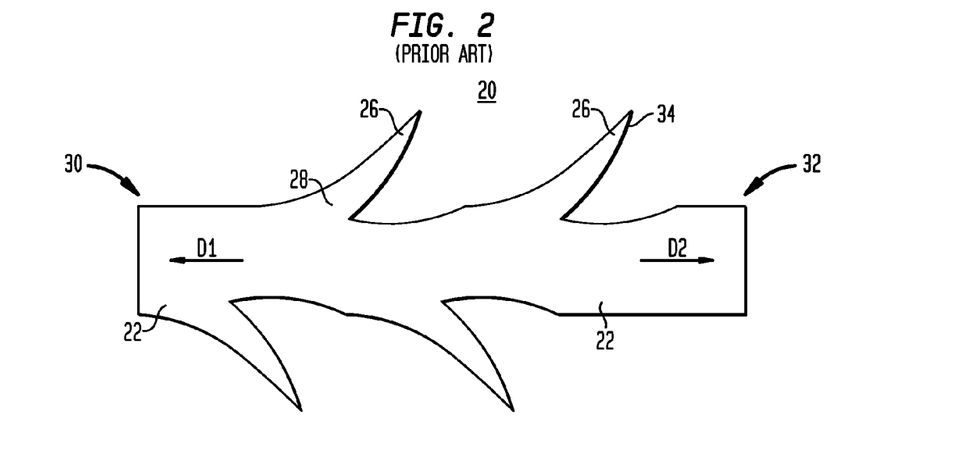
FIG. 2 shows another view of the prior art barbed suture of FIG. 1.

For example, referring to FIG. 2, after the cutting steps previously described, the cut barbs 24 remain flexibly coupled with the core thread 22 via the bases 28. When a leading end 30 of the barbed suture 20 is pulled in the direction D1, the barbs 24 collapse inwardly toward the core thread 22, and deflect toward a trailing end 32 of the barbed suture 20. When the trailing end 32 of the barbed suture is pulled in the direction $D_2$, trailing edges 34 of the barbs 26 penetrate and engage the surrounding media. Continued motion of the suture in direction $D_2$ causes the barbs to deflect outwardly and away from the core thread 22. As the barbed suture is pulled in the direction $D_2$, great stress builds upon the previously cut base sections 28. As a result, one or more of the barbs 26 may fail at the base sections 28 and delaminate from the core thread 22. This type of structural failure may result in catastrophic failure of the barbed suture, which may cause serious injury to, or the death of, a patient.

In order to improve the reliability and durability of barbed sutures, some have attempted to enhance the strength of the connection between the barbs and the core thread. Unfortunately, these efforts have provided barbed sutures that are rigid or relatively inflexible when deflecting in either direction. As a result, the rigid barbs resist the necessary collapsing deflection necessary when pulled through tissue and impart significant drag and damage to the tissue during passage. The drag and tissue damage effects become exaggerated when the barbed elements are in radial opposition to each other along the core thread. When the barbs are placed in radial opposition to each other, the projected cross section of the suture with the two rigid barbs extending from the core thread result in sawing of the tissue when the suture is applied. Due to this "sawing effect", the tissue may be damaged and the ultimate holding strength of the applied suture may be reduced.

In some instances, braided barbed sutures having more durable barbs are used. The braided barbed sutures include at least one barbed filamentary element intertwined with a plurality of unbarbed filaments to provide a barbed suture that is more rugged and durable. In one embodiment of commonly assigned U.S. Patent Application Publication No. 2007/0005110, the disclosure of which is hereby incorporated by reference herein, a prosthetic heart valve has a valve sewing ring and braided barbed sutures are disposed in the valve sewing ring by first passing the sutures through an annulus and then passing the sutures through the valve sewing ring. Approximately 12-20 sets of braided barbed sutures are passed through the valve sewing ring to secure the prosthetic heart valve in place. The heart valve is then parachuted down the sets of barbed sutures and seated in place within the annulus. After the heart valve has been parachuted down into place, the barbs prevent the valve from being moved in the opposite, upward direction for holding the heart valve in place without requiring knots. While the braided construction improves the durability of the suture, the process to produce the braided barbed suture is more extensive than the processes required for simple barbed monofilament suture.

In spite of the above advances, there remains a need for monofilament barbed sutures that may be readily manufactured and that have improved reliability, durability and efficacy. There also remains a need for barbed sutures that cause minimal or no damage to tissue as the suture is passed through the tissue while retaining their structural integrity. Moreover, there remains a need for barbed sutures that stay in place after being positioned in tissue and prosthetic devices.

SUMMARY OF THE INVENTION

In one embodiment, a barbed suture includes a flexible thread having a leading end, a trailing end, a central axis extending between the leading and the trailing ends, and an outer surface surrounding the central axis. The barbed suture desirably includes an elongated channel extending through the flexible thread between the outer surface and the central axis to define a flexible flap extending along the length of the flexible thread. The flexible flap has a base connected with a core section of the flexible thread and an outer, free end spaced from the base. A plurality of slots is desirably formed in the flexible flap for dividing the flexible flap into a plurality of barbs. In one embodiment, the slots are preferably angled toward the trailing end of the flexible thread. Each slot preferably extends outwardly from the core section of the suture and rearwardly toward the trailing end of the flexible thread. In one embodiment, each of the slots has a leading end that intersects with the outer surface of the flexible thread to define a pointed trailing end of each barb that faces toward the trailing end of the flexible thread.

In one embodiment, the pointed trailing ends of said barbs are normally aligned with the outer surface of the flexible thread and are collapsible inwardly toward the central axis of said flexible thread. In one embodiment, the barbs normally define an axial projection without a radial projection, whereby the barbs have outer surfaces that are common with the outer surface of the flexible thread.

In one embodiment, a barbed suture desirably includes a second elongated channel extending through the flexible thread between the outer surface and the central axis of the flexible thread to define a second flexible flap extending along the length of the flexible thread. The second flexible flap desirably includes a base connected with a core section of the flexible thread and an outer end spaced from the base. A plurality of second slots are desirably formed in the second flexible flap for dividing the second flexible flap into a plurality of second barbs, each of the second slots extending outwardly from the core section of the flexible thread and rearwardly toward the trailing end of the flexible thread. In one embodiment, the second slots are preferably angled toward the trailing end of the flexible thread. Each of the second slots desirably has a leading end that intersects with the outer surface of the flexible thread to define a pointed trailing end on each of the second barbs that faces toward the trailing end of the flexible thread.

In one embodiment, the first slots extend along a first group of axes that are substantially parallel to one another, and the second slots extend along a second group of axes that are substantially parallel to one another. In one embodiment, the first flexible flap preferably includes a first inner surface in communication with the first channel and the second flexible flap includes a second inner surface in communication with the second channel. The first and second inner surfaces desirably face in opposite directions from one another. In one embodiment, the first and second inner surfaces are spaced from one another by the core section. The first and second flaps and the core section desirably have an S-shaped profile when viewed in cross-section.

In one embodiment, the first and second inner surfaces of the flexible flaps define concave surfaces. The terminology "concave surface" is used broadly herein to include curved surfaces and surfaces having radial segments, as well as surfaces having non-radial shapes such as polygon geometries and other flat geometries that emulate concave shapes. The terminology "concave surface" may also be used to cover structures having a series of flat segments that emulate a concave surface.

In one embodiment, as the barbed suture is pulled in a first direction (e.g. toward the leading end of the flexible thread), the first and second flexible barbs are collapsed inwardly into the respective first and second channels and toward the core section of the flexible thread. The channels desirably provide space for the first and second barbs to collapse inwardly so as to minimize the outer diameter of the barbed suture as the barbed suture is pulled in the first direction. When the barbed suture is pulled through a medium such as tissue in an opposite direction, the pointed trailing ends of each barb preferably resist and/or halt movement of the barbed suture in the second direction by penetrating and engaging the tissue. In one embodiment, when the barbed suture is pulled rearwardly, the pointed trailing ends of the first and second barbs flare outwardly upon engaging the medium so that the barbed suture has a larger outer diameter than when being pulled in the first direction.

In one embodiment, a barbed suture includes a flexible thread having a core with a leading end, a trailing end, and a central axis extending between the leading and the trailing ends. The barbed suture includes a first flexible flap having a first base connected with the core and a first free end spaced from the first base. The first flexible flap desirably extends between the leading and trailing ends of the core section and has a first inner surface spaced from the core section by a first elongated channel. The barbed suture desirably includes a second flexible flap having a second base connected to the core and a second free end spaced from the second base. The second flexible flap preferably extends between the leading and trailing ends of the core section and has a second inner surface spaced from the core section by a second elongated channel. The first and second inner surfaces of the flexible flaps may define concave surfaces. The barbed suture desirably has a plurality of first slots formed in the first flexible flap for dividing the first flexible flap into a plurality of first barbs, whereby each of the first slots extends outwardly from the core and rearwardly toward the trailing end of the core. The barbed suture preferably includes a plurality of second slots formed in the second flexible flap for dividing the second flexible flaps into a plurality of second barbs, whereby each of the second slots extends outwardly from the core and rearwardly toward the trailing end of the core.

In one embodiment, each of the first slots has a leading end that intersects with the outer surface of the flexible thread so as to define pointed trailing ends on each of the first barbs. The pointed trailing ends desirably face toward the trailing end of the core. Each of the second slots also desirably has a leading end that intersects with the outer surface of the flexible thread so as to define a pointed trailing end on each of the second barbs that face toward the trailing end of the core.

In one embodiment, the first inner surface on the first flexible flap and the second inner surface on the second flexible flap face in opposite directions. In one embodiment, the first elongated channel desirably extends through a first section (e.g. an upper half) of the flexible thread and the second elongated channel extends through a second section (e.g. a lower half) of the flexible thread. In one embodiment, the first flexible flap desirably has an outer surface that defines a first part of the outer surface of the flexible thread and the second flexible flap has an outer surface that defines a second part of the outer surface of the flexible thread. The outer surfaces of the first and second flexible flaps may define convexly curved surfaces. The terminology "convexly curved" is used broadly herein to include curved and radial surfaces, as well as surfaces having non-radial shapes such as polygon geometries and other flat geometries that emulate convex shapes. The terminology "convex surface" may also be used to cover structures having a series of flat segments that emulate a convex surface.

In one embodiment, the flexible thread preferably has a S-shaped cross-sectional profile with the first flexible flap forming a first part of the S and the second flexible flap forming a second part of the S. The first and second barbs are preferably adapted to collapse inwardly into the respective first and second channels and toward the core when the barbed suture is pulled in a first direction (e.g. toward the leading end of the core).

In one embodiment, a barbed suture desirably includes a flexible thread having a S-shaped cross-sectional profile including a core having a leading end and a trailing end, a first flexible flap projecting from the core and forming a first part of the S and a second flexible flap projecting from the core and forming a second part of the S. A plurality of first slots are desirably formed in the first flexible flap for defining first barbs projecting from the core, whereby each of the first slots extends outwardly from the core and rearwardly toward the trailing end of the core. The barbed suture desirably includes a plurality of second slots formed in the second flexible flap for defining second barbs projecting from the core, whereby each of the second slots extends outwardly from the core and rearwardly toward the trailing end of the core.

In one embodiment, the barbed suture includes a first elongated channel extending between the core and the first flexible flap and a second elongated channel extending between the core and the second flexible flap. The first and second elongated channels desirably provide space for the first and second barbs to collapse inwardly toward the core as the core is pulled through a medium in a first direction (e.g. toward the leading end of the core).

In one embodiment, the barbed suture is extruded. The barbed suture may be extruded having a S-shaped profile when viewed in cross-section. In another embodiment, the barbed suture is extruded as a round or oval shape when viewed in cross-section, and cuts are made in the suture to define the first and second channels, the first and second flexible flaps, and/or the first and second angled slots shown and described above. In one embodiment, the barbed suture may be extruded as a structure having a relatively flat rhombus cross-section that is subsequently formed through a second operation to define a first channel and a second channel. In another embodiment, the suture may be extruded as a structure having a "U" shaped profile with a thick base when viewed in cross-section. In one embodiment, the barbed suture is made of a polymer material. The barbed suture may also be intertwined with one or more filaments for improving the structural integrity of the barbed suture.

In one embodiment, a fiber or thread is produced with an extruded "S" type profile or an oval fiber is formed and a secondary process is used to create the channels. The barbed elements may be formed with simplified cutting or punching tooling. Complex barb geometries are not required. In one embodiment, the thin wall of the outer portions of the "S" geometry allows the barbs to collapse inwards toward the central axis of the fiber when the element is pulled through tissue. This inward collapse, coupled with the angular punched slots, enables the overall projection of a relatively smooth profile to be pulled through the tissue and thus reduces sawing of the tissue. When the fiber is pulled in the reverse direction, the pointed ends of the cut geometry are able to engage the tissue. Due to the thin geometry located along the base of the "S" form, coupled with the disrupted edge from the punched slot, the barbed elements are able to deflect away from the central axis, thereby increasing the frictional drag to resist the reversing motion.

In one embodiment, a barbed suture includes a flexible thread having a leading end, and a trailing end, and a plurality of barbs projecting from the flexible thread. When not under strain or stress, the barbs normally project axially toward the trailing end of the flexible thread. In one embodiment, the barbs have an axial projection without a radial projection. The channels preferably enhance the flexibility of the barbs and provide space for the barbs to collapse inwardly toward the flexible thread as the leading end of the flexible thread is pulled through a medium, such as tissue or a prosthetic device.

In one embodiment, the barbed suture is extruded. The barbed suture preferably comprises a biocompatible material such as a biocompatible polymer. The barbs, the channels, and the slots in the flexible thread may be formed using a cutting or punching operation.

In one embodiment, a barbed suture includes a flexible thread having an outer surface and one or more channels extending between the outer surface and a center of the thread. As the leading end of the flexible thread is passed through a medium (e.g. tissue), the barbs are adapted to collapse inwardly into the channels and toward the center of the thread for minimizing the outer diameter of the barbed suture.

In one embodiment, each of the barbs is connected to the flexible thread by a base section, and the base section of at least one of the barbs has a crease formed therein for enhancing the flexibility of the barbs. In one embodiment, each of the barbs has a crease formed therein for enhancing the flexibility of the barbs so as to minimize drag and/or the "sawing" effect as the barbed suture is pulled through a medium such as tissue. In one embodiment, the flexible thread has a longitudinal axis that extends between the leading and trailing ends thereof and the creases extend in planes that are substantially parallel with the longitudinal axis.

In one embodiment, a barbed suture includes a flexible thread having a leading end, and a trailing end, and a plurality of barbs projecting from the flexible thread and extending toward the trailing end of the flexible thread, whereby each barb includes a base connected with the flexible thread and a tip remote from the base. The flexible thread preferably has one or more channels extending along the length of the thread, whereby each of the channels is disposed adjacent the base of one of the barbs. The channels enhance the flexibility of the barbs, particularly at the bases of the barbs, thereby minimizing drag as the barbed suture is passed through a medium (e.g. tissue). The channels also minimize the likelihood of the "sawing effect" discussed above. In addition, the channels are preferably adapted to provide space for the barbs when the barbs collapse inwardly toward the center of the flexible thread for minimizing the outer diameter of the barbed suture.

In one embodiment, the plurality of barbs project axially along the length of the flexible thread without a radial projection outward from the outermost perimeter, or axial wall, of the thread. As a result, in a normal unstressed configuration, the outer surfaces of the barbs and the tips of the barbs define an outer diameter or dimension that is no greater than the outer diameter of the suture that precedes or follows the barb. In other words, the outer diameter of the suture is no greater at the barbed sections than the un-barbed sections, and the barbed sections have outer surfaces that extend axially without a radial projection. Thus, in one embodiment, the present invention minimizes and/or avoids any of the sawing effects noted in the prior art barbed sutures. Moreover, the barbed sutures are free to collapse inwardly into the channels and/or the core section of the thread or filament to minimize the outer diameter of the suture as the suture is passed through media.

In one embodiment, a core of a flexible thread has a longitudinal axis extending between the leading and trailing ends thereof, and the flexible thread has an outer surface that surrounds and extends along the longitudinal axis of the core. The barbs preferably have outer surfaces that are defined by the outer surface of the flexible thread, and the outer surfaces of the barbs normally extend along axes that are substantially parallel with the longitudinal axis of the core.

In one embodiment, a flexing element for preflexing the barbs toward the trailing end of a flexible thread includes a leading face, a trailing face, and a barb flexing opening extending between the leading and trailing faces thereof. The barb flexing opening has a smaller diameter than the outer diameter of the barbed suture when the barbs are in their normal, unstressed or unstrained state. The barb flexing opening of the flexing element is adapted to force the barbs inwardly toward the flexible thread as the leading end of the flexible thread is pulled through the barb flexing opening. In one embodiment, the barb flexing opening tapers inwardly between the leading and trailing faces of the barb flexing element. In one embodiment, the flexing element collapses the flanged portion of the fiber and the barbs inwardly toward the central core to reduce the cross-section of the entire filament.

The barbs may be arranged on the flexible thread according to any desired configuration, and may be formed using any suitable method including those well known in the art. These methods may include stamping, punching, cutting by knife or laser, etching, press forming or the like.

These and other preferred embodiments of the present invention will be described in more detail below.

DETAILED DESCRIPTION

Conventional barbed sutures tend to be rigid and relatively inflexible. Prior art attempts to improve the flexibility of barbs has often resulted in barbed sutures having barbs that easily delaminate from a core thread or filament of the suture, or barbs that exhibit inadequate load bearing properties due to increased barb flexibility. Other attempts to prevent delamination have produced rigid barbs that do not flex/collapse easily when pulled through media, which can impart significant drag and "sawing effect" media damage during passage. In addition, the drag and media damage effects become exaggerated when the barbed elements radially oppose each other along the length of the suture.

Although the present invention is not limited by any particular theory of operation, it is believed that the barbed suture disclosure herein may be pulled through tissue with minimal "sawing effect" and with no loss of core thread strength due to providing a barbed suture having thin walled barbs that undergo three dimensional bending and are formed of a non-planar cross-sectional profile for minimizing the rigidity of the barbs when the suture is passed through tissue. In addition, the present invention provides barbed sutures having channels formed between the outer surface of the thread and the center of the thread for providing a seating area for the barbs to collapse inwardly as the barbs pass through media so that the outer diameter of the barbed sections (when the barbs are collapsed) is no greater than the diameter of the non-barbed sections. In addition, the channels enhance the flexibility of the barbs so as to enable the barbs to more easily collapse inwardly when being pulled through media. The channels also provide space for the inwardly collapsing barbs so that the outer diameter of a collapsed barbed section is no greater than the outer diameter of a non-barbed section.

Figure 3A:
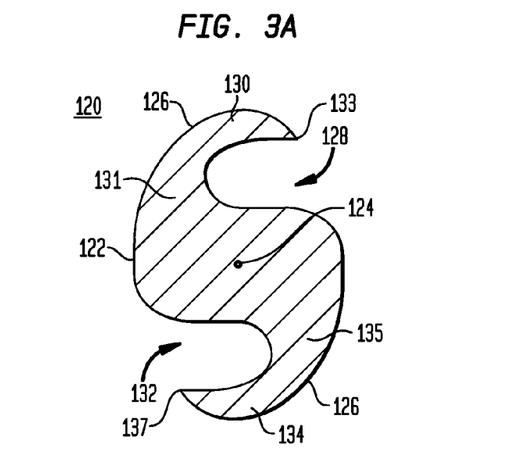
FIG. 3A shows an end view of a barbed suture, in accordance with one embodiment of the present invention.
Figure 3B:
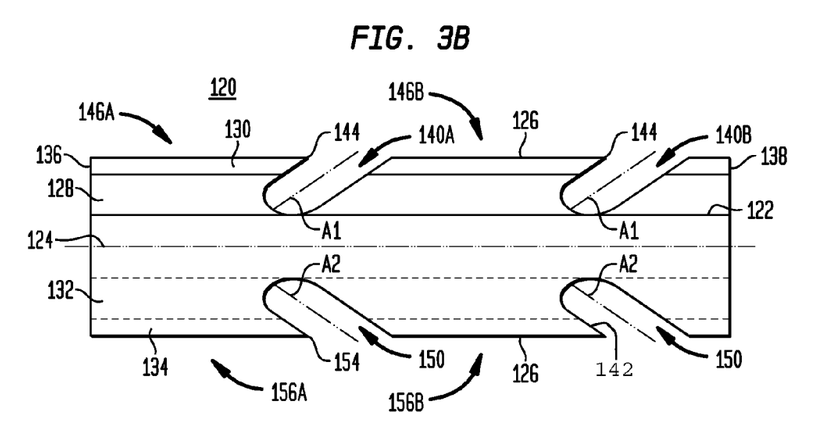
FIG. 3B shows a side elevational view of the barbed suture shown in FIG. 3A.

Referring to FIGS. 3A and 3B, in one embodiment, a barbed suture 120 has an S-shaped profile when viewed in cross-section. The barbed suture 120 includes a flexible thread 122 having a central axis 124 and an outer surface 126 that surrounds the central axis 124. The flexible thread 122 preferably includes a first elongated channel 128 formed therein that extends along the length of the flexible thread between the central axis 124 and the outer surface 126 thereof. The channel may be cut into or formed in the thread, or the thread may be extruded with the channel in place. The first channel 128 defines a first flexible flap 130 that is collapsible inwardly toward the central axis 124 of the flexible thread 122. In one embodiment, the first channel 128 desirably extends along an axis that is substantially parallel with the central axis 124.

In one embodiment, the flexible thread 122 includes a second elongated channel 132 formed therein that extends along the length of the flexible thread between the central axis 124 and the outer surface 126 of the flexible thread 122. The second channel may be formed using the same techniques for forming the first channel. The second channel 132 defines a second flexible flap 134 that is collapsible inwardly toward the central axis 124 of the flexible thread 122. In one embodiment, the second channel 132 desirably extends along an axis that is substantially parallel with the central axis 124.

In one embodiment, the barbed suture 120 is extruded and the extruded structure has a generally S-shaped profile as shown in FIG. 3A. In one embodiment, a barbed suture having a generally S-shaped profile may be formed by first providing an oval or round shaped flexible thread and then forming the first and second elongated channels 128, 132 in the thread. The channels preferably extend along the length of the flexible thread and extend substantially parallel with the central axis of the flexible thread.

Referring to FIG. 3B, in one embodiment, the flexible thread 122 includes a leading end 136, a trailing end 138, the first flexible flap 130 overlying the first channel 128, and the second flexible flap 134 overlying the second channel 132. The first and second channels 128, 132 extend along respective axes that are substantially parallel with the central axis 124 of the flexible thread 122. In one embodiment, the first channel extends through a first section of the thread and the second channel extends through a second section of the thread.

The first flexible flap 130 preferably has a base 131 secured to a core of the flexible thread and a free tip 133 remote therefrom. The second flexible flap 134 has a base 135 secured to the core and a free tip 137 remote therefrom.

The first flexible flap 130 desirably has a plurality of first angled slots 140A, 140B formed therein. Although only two angled slots 240 are shown in FIG. 3B, in other embodiments a plurality of angled slots (e.g. 50 or more) may be formed in the first flexible flap 130. The first angled slots 140A, 140B preferably extend along a first axis $A_1$ that forms an angle with the central axis 124. Each of the first axes $A_1$ preferably extend outwardly away from the central axis 124 and rearwardly toward the trailing end 138 of the flexible thread 122. A leading surface 142 of each first angled slot 140 preferably intersects with the outer surface 126 of the first flexible flap to define a pointed trailing end 144 of each barb 146. The angled slots 140A, 140B preferably define a plurality of first flexible barbs 146A, 146B, etc. that extend along a first section (e.g. an upper half) of the flexible thread 122.

The second flexible flap 132 desirably has a plurality of second angled slots 150A, 150B formed therein. Although only two of the second angled slots 150A, 150B are shown in FIG. 3B, in other embodiments a plurality of angled slots (e.g. 50 or more) may be formed in the second flexible flap 132. The second angled slots 150A, 150B preferably extend along a second axis $A_2$ that forms an angle with the central axis 124. Each of the second axes $A_2$ preferably extend outwardly away from the central axis 124 and rearwardly toward the trailing end 138 of the flexible thread 122. A leading surface 154 of each second angled slot 150 preferably intersects with the outer surface 126 of the second flexible flap 134 to define a pointed trailing end 154 of each second barb 156. The angled slots 150A, 150B preferably define a plurality of second flexible barbs 156A, 156B, etc. that extend along a second section (e.g. a lower half) of the flexible thread 122.

Figure 4A:
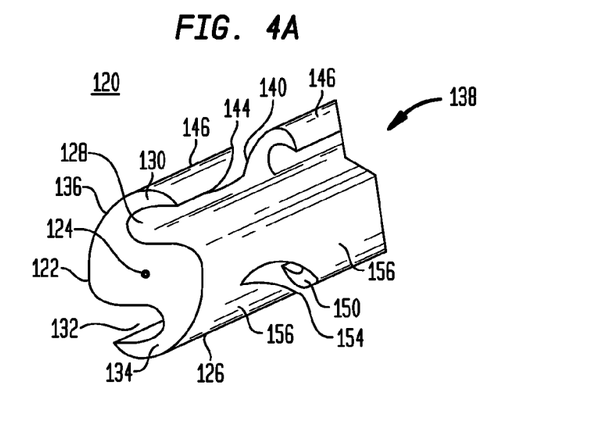
FIG. 4A shows a perspective view of the barbed suture of FIGS. 3A and 3B.

FIG. 4A shows a perspective view of the barbed suture 120 shown and described above in FIGS. 3A and 3B. The barbed suture 120 includes a flexible thread 122 having a central axis 124 and an outer surface 126 that surrounds the central axis 124. The flexible thread 122 extends between the leading end 136 and the trailing end 138 of the suture. First and second channels 128, 132 extend along the length of the flexible thread 122. The first channel 128 extends along the upper half of the flexible thread between the central axis 124 and the first flexible flap 130 and the second channel 132 extends along the lower half of the flexible thread between the central axis 124 and the second flexible flap 134. The flexible barb 120 includes first angled slots 140 formed in the first flexible flap 130 for defining a plurality of first flexible barbs 146 extending along the upper half of the flexible thread 122. The first angled slots 140 intersect with the outer surface 126 of the flexible thread 122 to define a pointed trailing end 144 on each of the first flexible barbs 146. The flexible thread 122 also includes second angled slots 150 that are formed in the second flexible flap 134 to define second flexible barbs 156 extending between the leading and trailing ends of the flexible thread 122. The second angled slots 150 intersect with the outer surface 126 of the flexible thread 122 to define pointed trailing ends 154 at the trailing ends of each of the second flexible barbs 156.

Figure 4B:
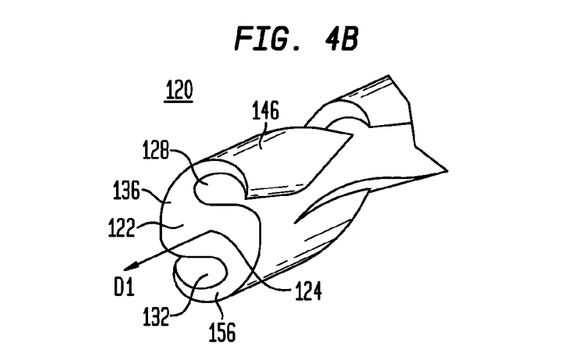
FIG. 4B shows the barbed suture of FIG. 4A being pulled through media toward a leading end of the barbed suture.

FIG. 4B shows the barbed suture 120 being pulled through tissue or media in the direction $D_1$, (e.g. toward the leading end 136 of the flexible thread 122). As the flexible thread 122 is pulled in the direction $D_1$, the plurality of first and second flexible barbs 146, 156 collapses inwardly into the respective first and second channels 128, 132 and toward the central axis 124 of the flexible thread 122. The first and second channels 128, 132 provide space for the respective first and second flexible barbs 146, 156 to collapse inwardly. As a result, the outer dimensions of the flexible barb 120 are minimized as the barb is pulled in the direction $D_1$ through media such as body tissue, which minimizes tissue damage.

Figure 4C:
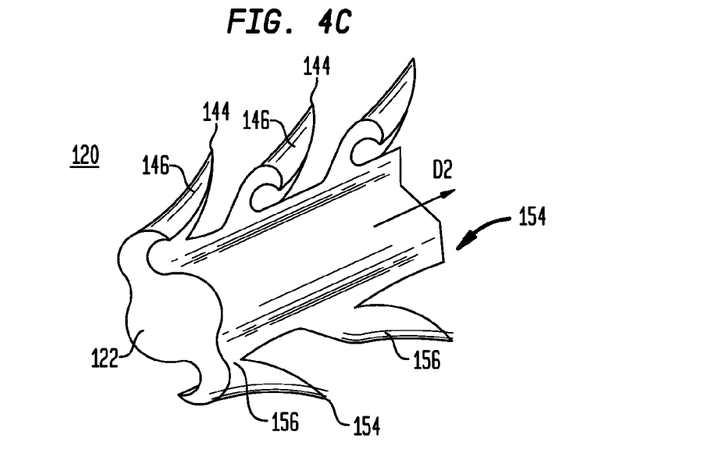
FIG. 4C shows the barbed suture of FIG. 4A being pulled through media toward a trailing end of the barbed suture.

After the flexible barb is embedded in media, tension or stress forces may be applied to the suture that pull the barbed suture in an opposite direction (e.g. toward the trailing end of the flexible thread). FIG. 4C shows the barbed suture 120 being pulled through tissue in an opposite direction $D_2$ from the direction shown in FIG. 4B. As the flexible thread 122 is pulled rearwardly in the direction $D_2$, the pointed ends 144, 154 of the respective first and second flexible barbs 146, 156 engage the tissue. As the pointed ends 144, 154 engage the tissue, the first and second flexible barbs 146, 156 flare outwardly to resist or halt movement of the flexible thread 122 in the rearward direction $D_2$.

Figure 5:
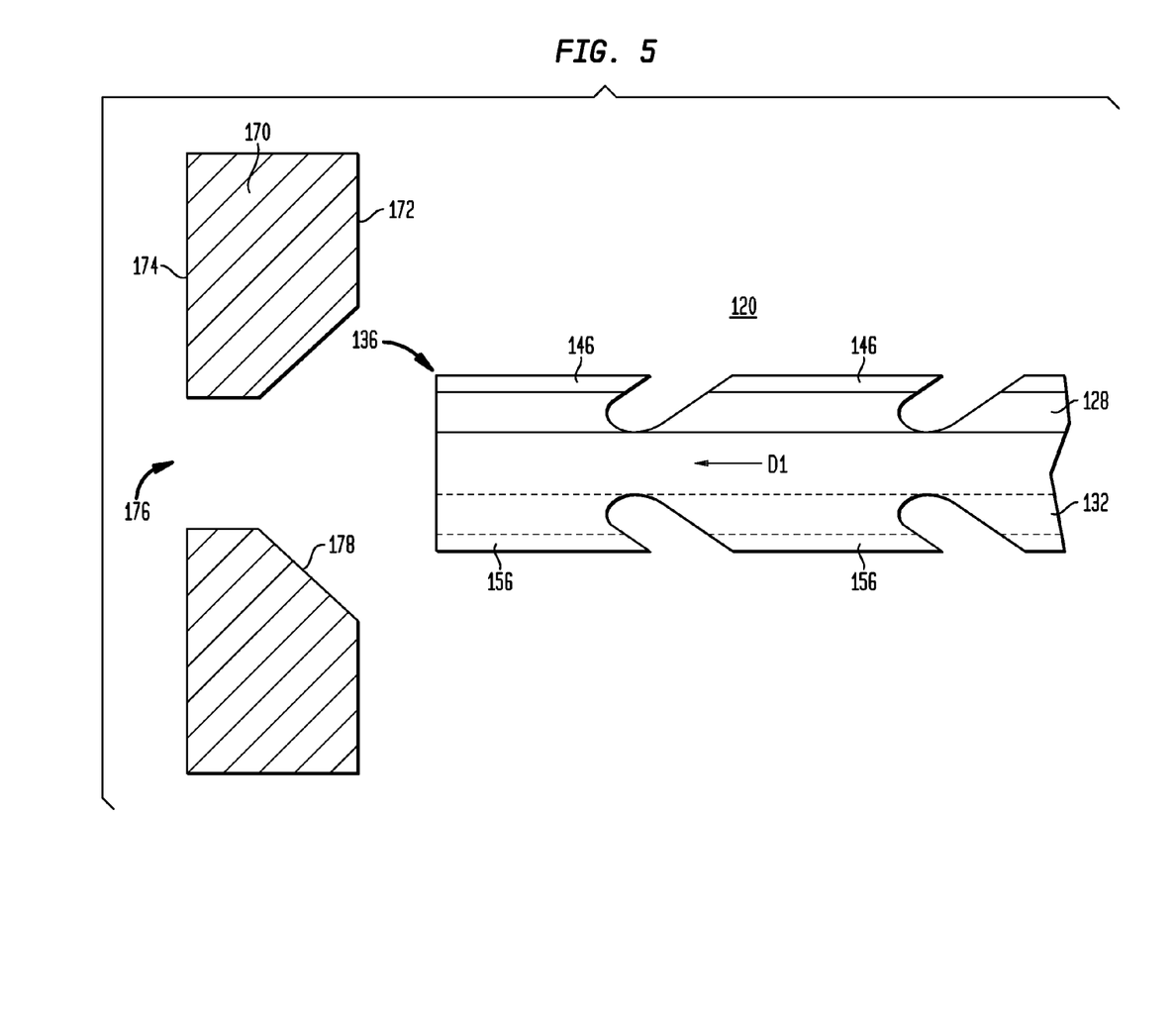
FIG. 5 shows a side view of a flexing element for preflexing the barbed suture shown in FIGS. 3A and 3B.

Referring FIG. 5, in one embodiment, the extruded profile and associated barbs 146, 156 may be pre-flexed by passing the barbed suture 120 through a flexing element 170. In one embodiment, the flexing element 170 includes a first face 172, a second face 174, and an opening 176 extending between the first and second faces 172, 174. The shape of the opening 176 in the first face 172 may include tapered walls 178. In order to pre-flex the extruded profile and associated barbs 146, 156 so as to produce a partial plastic deformation of the barbed suture 120, to provide a reduced profile of the fiber, a leading end 136 of the barbed suture 120 is passed through the tapered opening 176 and pulled in the direction indicated by arrow $D_1$. As the barbed suture 120 is pulled through the flexing element 170 in the direction $D_1$, the outer perimeter of the extruded profile 146, 156 engages the tapered opening 178 and collapses inwardly into the respective channels 128, 132 and toward the center of the flexible thread 122. As noted above, the channels 128, 132 provide space for the profile and associated barbs 146, 156 to flex and/or collapse inwardly so that when the barbed suture is pulled through tissue the likelihood of tissue damage is minimized. In one embodiment, the flexing element and/or the barbed suture may be heated before the barbed suture is passed through the opening 176 of the flexing element 170 so as to aid in pre-flexing the profile and associated barbs 146, 156, and to minimize the cross sectional profile and collapsibility of the barbed elements during application.

In one embodiment, a barbed suture of the present invention may be a bidirectional barbed suture having a first section having a first set of barbs and a first suture needle, and a second section having a second set of barbs and a second suture needle. The first set of barbs may extend in a different direction than the second set of barbs. In other preferred embodiments, the barbed suture may be a unidirectional barbed suture. In one embodiment, a barbed suture of the present invention may be used to secure a prosthetic device such as a prosthetic heart valve having a valve sewing ring, whereby the barbed suture is passed through tissue and the valve sewing ring.

In one embodiment, a tensioning device may be used for applying tension to the barbed sutures disclosed herein. The tensioning device may include one or more of the features disclosed in commonly assigned U.S. patent application Ser.

No. 12/135,176, filed Jun. 7, 2008, the disclosure of which is hereby incorporated by reference herein. Although the present invention is not limited by any particular theory of operation, it is believed that the tensioning device shown and described in the '176 application provides highly localized pressure on tissue and/or prosthetic devices where needed for tensioning barbed sutures. Thus, stretching of the tissue is reduced or eliminated and improved anchoring of the sutures, tissue and/or prosthetic devices will occur.

In one embodiment, creases may be formed in the bases of the barbs to ensure consistent and proper flexing of the barbed elements and to reduce the load necessary to ensure motion through the tissue in the direction of insertion. The creases formed in the barbs may extend in directions that are parallel to one another and parallel to a longitudinal axis of the barbed suture.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A barbed suture comprising:
   a flexible thread having a leading end, a trailing end, a central axis extending along the length of said flexible thread between the leading and the trailing ends, and an outer surface surrounding the central axis;
   a first elongated channel formed in and extending straight along the length of said flexible thread between the outer surface and the central axis of said flexible thread to define a first flexible flap extending along the length of said flexible thread, said first flexible flap having a base connected with a core section of said flexible thread and a free tip spaced from said base, wherein said first flexible flap, when said flexible thread is in an undeflected state, has a concave inner surface and a convex outer surface that defines the outer surface of said flexible thread; and
   a plurality of slots formed in said first flexible flap for dividing said first flexible flap into a plurality of barbs, each of said plurality of slots extending outwardly from the core section of said flexible thread and rearwardly toward the trailing end of said flexible thread, and each of said plurality of barbs including a portion of said concave inner surface and said convex outer surface of said first flexible flap.

2. The barbed suture as claimed in claim 1, wherein each of said plurality of slots has a leading surface that intersects with the outer surface of said flexible thread to define a pointed trailing end of one of said barbs that faces toward the trailing end of said flexible thread.

3. The barbed suture as claimed in claim 2, wherein the pointed trailing ends of said barbs are aligned with the outer surface of said flexible thread and are collapsible inwardly into the first elongated channel of said flexible thread.

4. The barbed suture as claimed in claim 2, further comprising:
   a second elongated channel formed in and extending along the length of said flexible thread between the outer surface and the central axis of said flexible thread to define a second flexible flap extending along the length of said flexible thread, said second flexible flap having a base connected with a core section of said flexible thread and a free tip spaced from said base, wherein said second flexible flap, when in an undeflected state, has a concave inner surface and a convex outer surface that defines the outer surface of said flexible thread;
   a plurality of second slots formed in said second flexible flap for dividing said second flexible flap into a plurality of second barbs, each of said plurality of second slots extending outwardly from the core section of said flexible thread and rearwardly toward the trailing end of said flexible thread, and each of said plurality of second barbs including a portion of said second concave inner surface and said second convex outer surface of said second flexible flap.

5. The barbed suture as claimed in claim 4, wherein each of said plurality of second slots has a leading surface that intersects with the outer surface of said flexible thread to define a pointed trailing end of one of said second barbs, and wherein the pointed trailing end of said one of said second barbs faces toward the trailing end of said flexible thread.

6. The barbed suture as claimed in claim 5, wherein said first slots extend along a first group of axes that are substantially parallel to one another and said second slots extend along a second group of axes that are substantially parallel to one another.

7. The barbed suture as claimed in claim 4, wherein said first flexible flap, when said flexible thread is in the undeflected state, includes said first concave inner surface in communication with said first channel and said second flexible flap, when said flexible thread is in the undeflected state, includes said second concave inner surface in communication with said second channel, wherein said first and second channels are parallel with the central axis, and wherein said first and second concave inner surfaces face in opposite directions from one another.

8. A barbed suture comprising:
   a flexible thread including a core having a leading end, a trailing end, and a central axis extending between the leading and the trailing ends;
   a first flexible flap having a first base connected to said core and a first free end spaced from said first base, said first flexible flap extending between the leading and trailing ends of said core section and, when said flexible thread is in an undeflected state, said first flexible flap has a first concave inner surface spaced from said core section by a first elongated channel extending straight along the length of said flexible thread;
   a second flexible flap having a second base connected to said core and a second free end spaced from said second base, said second flexible flap extending between the leading and trailing ends of said core section and, when said flexible thread is in an undeflected state, said second flexible flap has a second concave inner surface spaced from said core section by a second elongated channel extending straight along the length of said flexible thread;
   a plurality of first slots formed in said first flexible flap for dividing said first flexible flap into a plurality of first barbs, each of said plurality of first slots extending outwardly from said core and rearwardly toward the trailing end of said core, and each of said plurality of first barbs including a portion of said first concave inner surface; and
   a plurality of second slots formed in said second flexible flap for dividing said second flexible flap into a plurality of second barbs, each of said plurality of second slots extending outwardly from said core and rearwardly toward the trailing end of said core, and each of said plurality of second barbs including a portion of said second concave inner surface.

9. The barbed suture as claimed in claim 8, wherein each of said plurality of first slots has a leading surface that intersects with the outer surface of said flexible thread to define pointed trailing ends on each of said plurality of first barbs that face toward the trailing end of said core, and each of said plurality of second slots has a leading surface that intersects with the outer surface of said flexible thread to define pointed trailing ends on each of said plurality of second barbs that face toward the trailing end of said core.

10. The barbed suture as claimed in claim 8, wherein said first and second concave inner surfaces face in opposite directions.

11. The barbed suture as claimed in claim 8, wherein said first elongated channel extends through a first section of said flexible thread and said second elongated channel extends through a second section of said flexible thread, and wherein said first and second elongated channels extend straight along the full length of said flexible thread and parallel to the central axis of said flexible thread.

12. The barbed suture as claimed in claim 8, wherein said first flexible flap has a convex outer surface that defines a first part of an outer surface of said flexible thread and said second flexible flap has a convex outer surface that defines a second part of the outer surface of said flexible thread.

13. The barbed suture as claimed in claim 8, wherein said flexible thread, when in the undeflected state, has an S-shaped cross-sectional profile with said first flexible flap forming a first part of the S-shaped profile and said second flexible flap forming a second part of the S-shaped profile.

14. The barbed suture as claimed in claim 8, wherein each of said plurality of first and second barbs are adapted to collapse inwardly into said respective first and second channels and toward said core when said barbed suture is pulled toward the leading end of said core.

15. A barbed suture comprising:
a flexible thread having a S-shaped cross-sectional profile when said flexible thread is in an undeflected state, said undeflected flexible thread including a core having a leading end and a trailing end, a first flexible flap projecting from said core, said first flexible flap, when said flexible thread is in the undeflected state, having a first concave inner surface extending along the length of said flexible thread and forming a first part of the S-shaped profile and a second flexible flap projecting from said core, said second flexible flap, when said flexible thread is in the undeflected state, having a second concave inner surface extending along the length of said flexible thread and forming a second part of the S-shaped profile;
a plurality of first slots formed in said first flexible flap for defining first barbs projecting from said core, each of said plurality of first slots extending outwardly from said core and rearwardly toward the trailing end of said core, and each of said plurality of first barbs including a portion of said first concave inner surface of said first flexible flap;
a plurality of second slots formed in said second flexible flap for defining second barbs projecting from said core, each of said plurality of second slots extending outwardly from said core and rearwardly toward the trailing end of said core, and each of said plurality of second barbs including a portion of said second concave inner surface of said second flexible flap.

16. The barbed suture as claimed in claim 15, further comprising:
a first elongated channel extending straight along the length of said flexible thread between said core and said first flexible flap; and
a second elongated channel extending straight along the length of said flexible thread between said core and said second flexible flap, wherein said first and second elongated channels provide space for said first and second barbs to collapse inwardly toward said core as the leading end of said core is pulled through a medium.

17. The barbed suture as claimed in claim 15, wherein said core has a longitudinal axis extending between the leading and trailing ends thereof, and said flexible thread has a round outer surface that surrounds and extends along the longitudinal axis of said core.

18. The barbed suture as claimed in claim 17, wherein said first and second barbs have convex outer surfaces that are defined by the outer surface of said flexible thread, and wherein the convex outer surfaces of said barbs extend along axes that are substantially parallel with the longitudinal axis of said core.

19. The barbed suture as claimed in claim 15, wherein said barbed suture is extruded and comprises a polymer.

20. The barbed suture as claimed in claim 15, wherein said first concave inner surface of said first flexible flap faces in a first direction and said second concave inner surface of said second flexible flap faces in a second direction that is opposite the first direction.

* * * * *